(12) United States Patent
Venturini

(10) Patent No.: US 6,949,100 B1
(45) Date of Patent: Sep. 27, 2005

(54) BONE SCREW FOR USE IN ORTHOPAEDIC SURGERY

(75) Inventor: Daniele Venturini, Povegliano Veronese (IT)

(73) Assignee: Orthofix S.r.l., Milan (IT)

( * ) Notice: Subject to any disclaimer, the term of this patent is extended or adjusted under 35 U.S.C. 154(b) by 0 days.

(21) Appl. No.: 09/937,941

(22) PCT Filed: Apr. 3, 2000

(86) PCT No.: PCT/EP00/02953

§ 371 (c)(1),
(2), (4) Date: Jan. 25, 2002

(87) PCT Pub. No.: WO00/61022

PCT Pub. Date: Oct. 19, 2000

(30) Foreign Application Priority Data

Apr. 8, 1999 (EP) .................................. 99830204

(51) Int. Cl.⁷ ............................................. A61B 17/84
(52) U.S. Cl. ..................................................... 606/73
(58) Field of Search ............................ 606/73, 65, 66, 606/72, 71, 61, 69, 76; 411/414, 411, 404

(56) References Cited

U.S. PATENT DOCUMENTS

| | | | |
|---|---|---|---|
| 3,915,162 A | | 10/1975 | Miller |
| 4,463,753 A | * | 8/1984 | Gustilo .......................... 606/73 |
| 4,544,313 A | * | 10/1985 | Grossberndt ................. 411/411 |
| 4,978,350 A | * | 12/1990 | Wagenknecht ................ 606/72 |
| 5,180,382 A | * | 1/1993 | Frigg et al. .................... 606/65 |
| 5,505,736 A | * | 4/1996 | Reimels et al. ............... 606/72 |
| 5,544,993 A | * | 8/1996 | Harle .......................... 411/414 |
| 5,643,269 A | * | 7/1997 | Harle ........................... 606/79 |
| 5,871,486 A | * | 2/1999 | Huebner et al. .............. 606/73 |

FOREIGN PATENT DOCUMENTS

| | | |
|---|---|---|
| DE | 43 29 788 A1 | 3/1995 |
| EP | 0 012 441 A1 | 6/1980 |
| FR | 1 266 386 A | 5/1961 |

\* cited by examiner

*Primary Examiner*—Pedro Philogene
(74) *Attorney, Agent, or Firm*—Leydig, Voit & Mayer, Ltd.

(57) ABSTRACT

The invention relates to an improved bone screw for use in orthopaedic surgery, in particular with external fracture fixation devices, of the type which comprises ahead (3), a shank (4), and a threaded portion (5) tapering towards a tip (2) at the opposite end from the head (3). Advantageously, the threaded portion (5) has at least one constant pitch section comprising threads (9) which have a triangular cusp-like profile in cross section and are separated from each other by a shaped bottom land with a concave profile (10) defined by two countersloping planes.

10 Claims, 1 Drawing Sheet

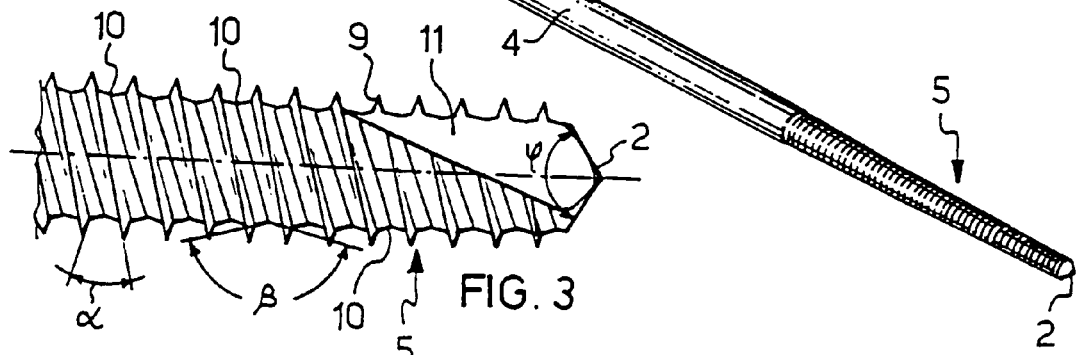
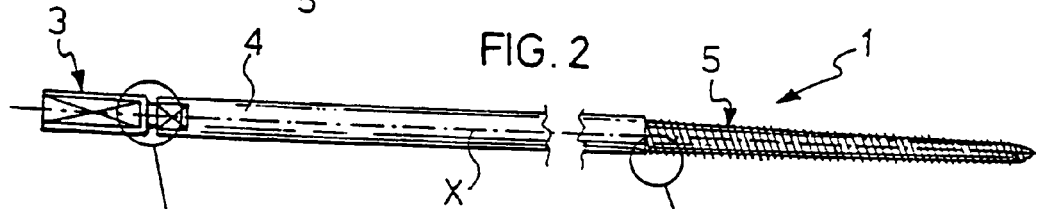
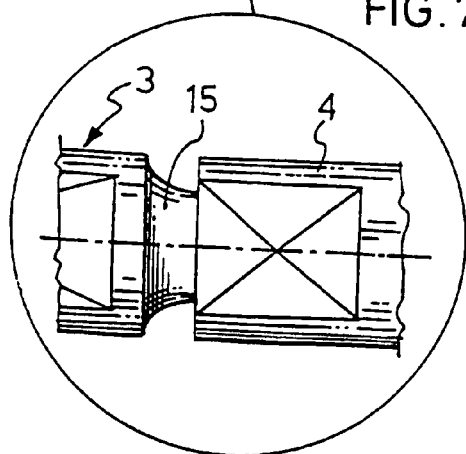
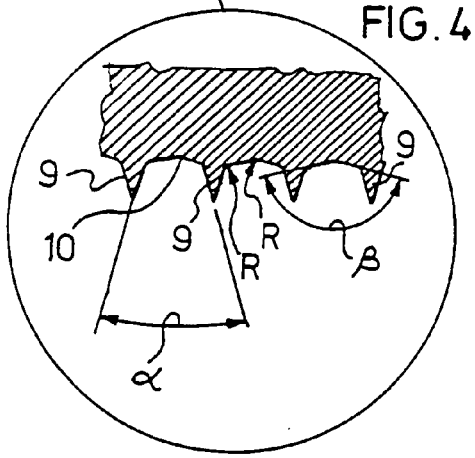
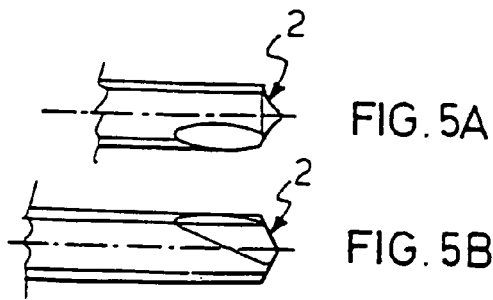
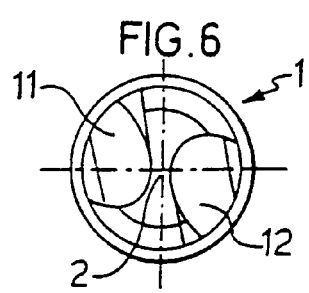

United States Patent US 6,949,100 B1

BONE SCREW FOR USE IN ORTHOPAEDIC SURGERY

TECHNICAL FIELD

This invention relates to an improved bone screw for use in orthopaedic surgery, specifically in devices for the external fixation of bone fractures.

More particularly, the invention relates to a screw having a head or application end, a shank, and a threaded portion, which tapers towards a tip at the opposite end from the application end.

BACKGROUND ART

As is well known, a variety of external fixation devices are currently employed with increasing frequency in human as well as veterinary orthopaedic surgical procedures for treating complex fractures and/or fractures associated with serious damage to the cutaneous tissue.

Devices of this kind allow broken bones to be consolidated and reduced in highly critical areas of the human bony structure, especially near joints.

Customarily, the opposite ends of an external fixation device are secured to respective undamaged portions of a broken bone by means of bone screws set in the bone itself. Such is the case, for example, with a tibial fixation device having opposite ends firmly secured across the fracture to the shinbone.

In other cases, such as when the fracture affects a joint, the bone screws are set in bones adjacent to the joint. This is done, for example, with an ankle external fixation device by setting the bone screws in the tibia and the talus.

The effectiveness of such devices improves with the holding power of their bone screws. In some cases, the screws extend transversely through the bone to affect entrance and exit cortical regions.

A comprehensive literature exists in this specific technical field on research work directed to determine the critical parameters that control the holding power of bone screws.

As an example, it has been found that a relatively fine thread improves the holding power of the screw, as described in an article "Cortical profile external fixation screw maintains torque in the metaphysis", Anatomy, Bristol, Jun. 17, 1996.

A radial preload on the screw prevents or attenuates the problem of the loss of grip or lysis in the first and/or the second cortical portion of the bone, as described in an article "Introduction and prevention of pin loosening in external fixation", Journal of Orthopaedic Trauma, Vol. 5, No. 4, pages 485–492.

Furthermore, providing a hole in the bone prior to inserting the screw, according to the screw diameter, lowers the insertion temperature which, if excessively high, can hurt the particular bone connective tissue around the screw, as described in an article "Cancellous Bone Screw Thread Design and Holding Power", Journal of Orthopaedic Trauma, Vol. 10, No. 7, pages 462–469.

The foregoing considerations lead to conclude that the holding power of a bone screw may be dependent on a series of features having a synergic combined effect.

However, application studies carried out at the Applicant's have resulted in the thread profile being identified as the fundamental factor of the screw holding power in the bone.

In particular, it has been found that conventional thread profiles have a common drawback in that they only provide an inferior distribution of C the stress from the force applied to penetrate the cortical portion of the bone.

In addition, conventional bone screws are of greater bulk for a given area of bone interface.

The underlying technical problem of this invention is to provide an improved bone screw having such structural and functional features as to effectively produce a self-tapping penetrative action during its insertion in the bone, and exhibiting improved holding power once in place, thereby overcoming all the drawbacks discussed hereinabove in connection with the prior art.

DISCLOSURE OF INVENTION

The concept of this invention is one of providing a bone screw with a self-tapping threaded portion which includes at least one constant pitch section comprised of threads having a triangular cusp profile in cross- section and being separated from each other by a shaped bottom land with a concave profile defined by two countersloping planes. This allows the elongate conical profile of the threaded portion to be put to best use, and affords a large area of contact with the bone effective to reduce the specific loading pressure.

Based on this concept, the technical problem is solved by a bone screw as previously indicated and defined in the characterising portions of claim 1 following.

The features and advantages of a bone screw according to the invention will be apparent from the following description of an embodiment thereof, given by way of non-limiting example with reference to the accompanying drawings.

BRIEF DESCRIPTION OF DRAWINGS

FIG. 1 is a perspective view showing schematically a bone screw according to this invention.

FIG. 2 is a schematic side elevation view of the screw shown in FIG. 1.

FIG. 3 shows schematically, drawn to an enlarged scale, a portion of the thread profile of the screw in FIG. 1.

FIG. 4 shows, drawn to a further enlarged scale, a detail of the thread profile of FIG. 3.

FIGS. 5A and 5B are respective enlarged views showing schematically the tip end of the screw of FIG. 1, as viewed from two different angles.

FIG. 6 is an enlarged front view showing schematically the tip end 11 S of the screw in FIG. 1.

FIG. 7 is a schematic detail view of the head end of the screw in FIG. 1.

MODES FOR CARRYING OUT THE INVENTION

Referring to the drawing views, in particular to the example of FIG. 1, generally and schematically shown at 1 is a bone screw according to this invention intended for use in human or animal orthopaedic surgery with devices for the external fixation of bone fractures.

The screw 1 has a tip end 2 adapted to be implanted by a surgeon into the cortical portion of a bone, and then driven in a threaded manner by means of a tool applied to a head end 3 of the screw.

The screw 1 comprises a shank 4 and a threaded portion 5 formed integral with the shank 4. The threaded portion 5 has an elongate conical shape and the same diameter as the shank 4 at its region adjoining the shank, to then taper slightly in the direction towards the tip end 2. The threaded portion 5 accounts for about one third of the screw overall length. However, another length ratio of the threaded portion 5 to the shank 4 could be chosen instead.

Advantageously, the screw is of the self-tapping type in that it is formed with a helical thread pattern which can be termed directional in the sense that it will retain its drive direction more effectively even when applied a high torque.

FIG. 3 is an enlarged view of the profile of the threaded portion 5 according to the invention.

Advantageously, the threaded portion has at least a section formed with a constant pitch, preferably a 1.25 mm pitch, and comprises threads 9 having a triangular profile in cross-section with a cusp or acute apex angle of 15° to 30°.

The facing walls of two adjacent threads form an acute angle α of conical convergence towards the longitudinal axis X of the screw. In the embodiment of FIG. 4, this angle is preferably no more than 30°.

Advantageously, the bottom land of the threads is shaped with a concave cross-section 10 between adjacent threads 9, effective to ease the material flow and relieve bone stress during the screw penetration.

The concave 10 is defined by two countersloping planes forming in cross-section an obtuse angle β of conical convergence towards the longitudinal axis of the screw. This obtuse angle is in the 120° to 150° range, preferably of 150° in the embodiment of FIG. 3.

The region between the inner walls and the bottom land of the threads 9 is radiused to a radius of 0.2 mm.

The thread height is three fifths the pitch, i.e. 0.75 mm. It is constant along the profile 5.

This thread allows the conical profile to be used at its best by concentrating the drag in the opposite direction to the driving/piercing direction.

By way of illustration only, the screw 1 may have an overall length of 175 mm, inclusive of 60 mm of threaded portion 5.

A variety of lengths may be contemplated to provide the surgeon with a range of bone screws to use according to necessity. For example, a suitable range might include screws with an overall length of 140 mm, including 40 mm of threaded portion; or screws 210 mm long with a 70 mm threaded portion; or screws 255 mm long with a threaded portion of at least 80 mm.

Where the screw is 175 mm long, the shank diameter is preferably of 6 mm, same as the outside diameter of the threaded portion 5 at the shank 4. At the tip end 2, the outside diameter of the threaded portion becomes 4 mm.

Accordingly, the core diameter of the threaded portion (i.e. the diameter at the base of the thread) will be 4.5 mm at the shank and 2.5 mm at the tip. Hence, in this case the ratio between the outside diameter of the threaded portion and the core diameter ranges from 1.43 mm at the shank (6 mm/4.5 mm) (4.0 mm/2.5 mm) and 1.6 at the tip (4 mm/2.5 mm).

Advantageously, the tip 2 of the screw 1 is formed with a pair of oppositely located grooves 11, 12 cut by straight-line milling.

The grooves extend at a predetermined inclination angle (p with respect to the longitudinal axis of the screw 1, and interfere with an end section of the threaded portion 5 near the tip.

The inclination angle φ is preferably of 150°.

The provision of such a groove pair allows the screw to be readily started into a hole pre-drilled through the bone, but also allows the section of the threaded portion that adjoins the tip and has not been removed to interfere with the second cortical portion of the bone.

To complete this description, it should be added that an annular groove 15 is provided near the head 3 of the screw 1 to facilitate cutting off a portion of the screw as may ultimately be protruding from the fixation device.

The screw of this invention is applied in a known manner in the art, with the one difference that the bone is pre-drilled in order to provide a suitable radial pre-load and keep the insertion temperature low.

Tests were conducted at the Applicant's, and finite element (FEM) calculations carried out on prototypes of a bone screw having the previously described thread profile.

The calculations were carried out to evaluate the effect of the two different thread profiles on a cancellous bone matrix in three distinct loading situations:

1) screw/bone interference;
2) pull-out force;
3) simulated actual loading.

It should be noted that the analysis of the stresses induced in the bone is not of absolute value, because of the bone being no linear elastic material. Accordingly, the values from the FEM analysis only become meaningful on a comparative basis, and in particular when compared with those for conventional bone screws used as references.

Loading situation (1) arises from the insertion of a thread having a 5 mm diameter (average of the conical diameter of the screw 1) and a thread height of 0.75 mm. This means that the core diameter of the threaded portion is 3.5 mm. A thread such as this was inserted through a 3.2 mm hole. Under these conditions, the screw is working at a so-called interference "i" given as: (screw core diameter−hole diameter)/2= (3.5−3.2)/2=0.15 mm.

Pull-out situation (2) applies to the threaded screw being subjected to a specific unit tension (p=1 N/mm²=1 MPa) in order to investigate its effect on a bonded cancellous bone. This situation simulates the pull-out effect in the absence of screw/bone interference, that is, similar to bone lysis situations.

Actual loading situation (3) is given by the combination of the previous two situations. In particular, a loading situation was simulated at an interference i=0.15 mm and a specific pull-out force of 8.5 MPa.

Now, the results of the FEM analysis, which have been summarized herein not to overburden the rest of the description, show that the screw of this invention distributes the stress better than conventional screws.

Furthermore, the pattern of the highest compressive stress from the pulling out shows that the screw of this invention transfers the stress onto several threads, whereas with conventional screws a single thread is mostly involved.

Finally, the screw of this invention shows to have a better distributed compression even in the absence of interference, that is in situations of an oversize pre-drilled hole, lysis or osteoporosis.

Thus, the bone screw according to the invention does solve the technical problem, and affords a number of advantages, outstanding among which is the fact that the thread profile of the screw allows the bone stress to be optimised, both as a result of the large area of contact with the bone and of the possibility given to the bony material to relax into the concave root lands of the threads. This allows the specific pressure under loading and the torque for screw penetration to be smaller.

What is claimed is:

1. A bone screw for use in orthopaedic surgery with external fixture fixation devices comprising a head at one end, a single threaded portion at an opposite end, a non-threaded cylindrical shank between said head and threaded portion, said head having a non-threaded configuration for securement by an orthopaedic external fixation device, said threaded portion having an outside diameter and a core diameter which taper uniformly toward a tip at an end opposite from the head, said threaded portion having at least one constant pitch section, said threaded portion having threads formed with an acute angle generally triangular cross-sectional profile, said threads being separated from each other by a shaped bottom land having a concave profile defined by two countersloping planes, said threads having a constant height with the ratio of the outside diameter to said core diameter within a range of 1.43 to 1.60, and said threaded portion and head having diameters no greater than the diameter of said shank.

2. A bone screw according to claim 1 characterised in that said shaped bottom land has in cross-section an obtuse angle ($\beta$) of conical convergence towards the longitudinal axis of the screw.

3. A bone screw according to claim 2, characterised in that said obtuse angle ($\beta$) is an angle of at least 150 °.

4. A bone screw according to claim 1, in which the acute angle of the cross-sectional profile of said teeth is in the range of 15° to 30°.

5. A bone screw according to claim 1, characterised in that said constant pitch is of 1.25 mm.

6. A bone screw according to claim 1, characterised in facing walls of adjacent threads have in cross-section an acute angle ($\alpha$) of conical convergence towards the longitudinal axis of the screw.

7. A bone screw according to claim 6, characterised in that said acute angle ($\alpha$) is an angle in the 15° to 30° range.

8. A bone screw according to claim 1, characterised in that the threaded portion (5) accounts for one third of the screw length.

9. A bone screw according to claim 1, characterised in that the height of the thread is three fifths the pitch length.

10. A bone screw according to claim 9, characterised in that said height is 0.75 mm.

* * * * *